United States Patent
Adams et al.

(10) Patent No.: US 10,363,065 B2
(45) Date of Patent: Jul. 30, 2019

(54) MEDICAL DEVICES AND METHODS FOR MANIPULATING BODILY TISSUES

(71) Applicant: Boston Scientific Scimed, Inc., Maple Grove, MN (US)

(72) Inventors: Kenneth W. Adams, Wilmington, MA (US); Kenneth M. Flynn, Woburn, MA (US); Peter S. Finamore, Douglaston, NY (US); Andrew Dolan, Bridgewater, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 319 days.

(21) Appl. No.: 14/514,003

(22) Filed: Oct. 14, 2014

(65) Prior Publication Data
US 2015/0105792 A1 Apr. 16, 2015

Related U.S. Application Data

(60) Provisional application No. 61/891,194, filed on Oct. 15, 2013.

(51) Int. Cl.
*A61B 17/42* (2006.01)
*A61B 17/02* (2006.01)

(52) U.S. Cl.
CPC .......... *A61B 17/42* (2013.01); *A61B 17/0218* (2013.01); *A61B 2017/4216* (2013.01); *A61B 2017/4225* (2013.01)

(58) Field of Classification Search
CPC .............................. A61B 17/42; A61B 17/4241
See application file for complete search history.

(56) References Cited

U.S. PATENT DOCUMENTS

| 1,615,728 A | 1/1927 | Smith |
| 3,580,313 A | 5/1971 | McKnight |
| 3,809,091 A * | 5/1974 | Shute .................. A61B 17/4241 606/119 |
| 4,048,987 A | 9/1977 | Hurson |
| 4,226,228 A | 10/1980 | Shin |
| 4,241,912 A | 12/1980 | Mercer |
| 4,574,791 A * | 3/1986 | Mitchener .............. A63B 23/20 482/122 |
| 4,747,393 A | 5/1988 | Medwid |
| 4,784,150 A | 11/1988 | Voorhies |

(Continued)

FOREIGN PATENT DOCUMENTS

| DE | 202004015215 U1 | 12/2004 |
| FR | 2817731 A1 | 6/2002 |

(Continued)

OTHER PUBLICATIONS

Puntambekar, et al, "A Novel Technique of Uterine Manipulation in Laparoscopic Pelvic Oncosurgical Procedures: The Uterine Hitch Technique", Nov. 26, 2009, 6 pages.

*Primary Examiner* — Richard G Louis
(74) *Attorney, Agent, or Firm* — Brake Hughes Bellermann LLP

(57) ABSTRACT

A medical device includes an elongate member. The elongate member has a first end portion and a second end portion. The second end portion of the elongate member has an upper surface and a lower surface disposed opposite the upper surface. The lower surface has a planar portion. The upper surface has a planar portion and a concave portion.

18 Claims, 14 Drawing Sheets

(56) References Cited

U.S. PATENT DOCUMENTS

| | | | |
|---|---|---|---|
| 4,881,526 A | 11/1989 | Johnson | |
| 5,104,377 A * | 4/1992 | Levine | A61M 25/1011 604/100.01 |
| 5,209,754 A | 5/1993 | Ahluwalia | |
| 5,217,463 A | 6/1993 | Mikhail | |
| 5,352,220 A * | 10/1994 | Abidin | A61B 17/02 30/162 |
| 5,464,409 A * | 11/1995 | Mohajer | A61B 17/4241 600/227 |
| 5,483,832 A | 1/1996 | Pauser | |
| 5,518,503 A | 5/1996 | Rooney | |
| 5,520,703 A | 5/1996 | Essig | |
| 5,656,014 A * | 8/1997 | Rooney | A61B 90/30 600/240 |
| 5,709,646 A * | 1/1998 | Lange | A61B 17/02 600/203 |
| 5,785,640 A | 7/1998 | Kresch | |
| 5,803,902 A | 9/1998 | Sienkiewicz | |
| 5,954,713 A * | 9/1999 | Newman | A61B 17/3207 606/15 |
| 6,048,351 A | 4/2000 | Gordon | |
| 6,068,591 A | 5/2000 | Bruckner | |
| 6,165,108 A | 12/2000 | Ralston | |
| 6,264,676 B1 | 7/2001 | Gellman | |
| 6,379,315 B1 * | 4/2002 | Claren | A61B 10/02 600/570 |
| 6,394,939 B1 | 5/2002 | Stein | |
| 6,723,057 B1 * | 4/2004 | Pearce | A61B 10/0291 600/562 |
| 7,001,317 B2 | 2/2006 | Marcotte | |
| 7,037,255 B2 | 5/2006 | Inman | |
| 7,048,682 B2 | 5/2006 | Neisz | |
| 7,371,245 B2 | 5/2008 | Evans | |
| 7,611,454 B2 | 11/2009 | De | |
| 7,981,024 B2 | 7/2011 | Levy | |
| 9,282,956 B2 | 3/2016 | Fairneny | |
| 2002/0000233 A1 | 1/2002 | Jude | |
| 2002/0028980 A1 | 3/2002 | Thierfelder | |
| 2002/0116025 A1 | 8/2002 | Haab | |
| 2004/0153065 A1 | 8/2004 | Lim | |
| 2005/0000523 A1 | 1/2005 | Beraud | |
| 2005/0131393 A1 | 6/2005 | Chu | |
| 2005/0256530 A1 | 11/2005 | Petros | |
| 2005/0277948 A1 | 12/2005 | Cedars | |
| 2005/0278037 A1 | 12/2005 | Delorme | |
| 2006/0058578 A1 | 3/2006 | Browning | |
| 2006/0089525 A1 | 4/2006 | Mamo | |
| 2006/0100475 A1 | 5/2006 | White | |
| 2006/0195007 A1 | 8/2006 | Anderson | |
| 2006/0217589 A1 | 9/2006 | Wan | |
| 2006/0229596 A1 | 10/2006 | Weiser | |
| 2007/0015953 A1 | 1/2007 | MacLean | |
| 2007/0060795 A1 | 3/2007 | Vayser | |
| 2007/0112361 A1 | 5/2007 | Schonholz | |
| 2007/0161849 A1 | 7/2007 | Goldberg | |
| 2007/0282223 A1 * | 12/2007 | Larkin | A61B 10/02 600/570 |
| 2008/0011107 A1 * | 1/2008 | Leventhal | B01L 3/18 73/864 |
| 2008/0039678 A1 | 2/2008 | Montpetit | |
| 2008/0081952 A1 | 4/2008 | Josephberg | |
| 2008/0221384 A1 | 9/2008 | Chi Sing | |
| 2009/0171143 A1 | 7/2009 | Chu | |
| 2009/0209973 A1 | 8/2009 | East | |
| 2009/0281377 A1 | 11/2009 | Newell | |
| 2010/0137692 A1 | 6/2010 | Lindsay | |
| 2010/0286482 A1 | 11/2010 | Rosenblatt | |
| 2010/0305394 A1 | 12/2010 | Rosenblatt | |
| 2010/0312051 A1 | 12/2010 | Brown | |
| 2011/0112372 A1 * | 5/2011 | Hajarian | A61M 1/008 600/205 |
| 2012/0016185 A1 | 1/2012 | Sherts | |
| 2012/0310250 A1 * | 12/2012 | McCue | A61B 17/42 606/121 |
| 2013/0005543 A1 | 1/2013 | Armitage | |
| 2013/0072749 A1 * | 3/2013 | Fairneny | A61B 17/02 600/37 |
| 2013/0197537 A1 | 8/2013 | Fairneny | |

FOREIGN PATENT DOCUMENTS

| | | |
|---|---|---|
| GB | 1604168 A | 12/1981 |
| WO | 2009076616 A2 | 6/2009 |
| WO | 2013040022 A1 | 3/2013 |
| WO | 2014143626 A1 | 9/2014 |

* cited by examiner

MEDICAL DEVICES AND METHODS FOR MANIPULATING BODILY TISSUES

CROSS-REFERENCE TO RELATED APPLICATION

This application is a Nonprovisional of, and claims priority to, U.S. Patent Application No. 61/891,194, filed on Oct. 15, 2013, entitled "MEDICAL DEVICES AND METHODS FOR MANIPULATING BODILY TISSUES", which is incorporated by reference herein in its entirety.

BACKGROUND

Field

The present invention generally relates to medical devices and procedures, particularly devices and methods used during surgery to manipulate bodily tissue.

Various types of tissue manipulators are used for manipulating pelvic and other organs to facilitate access to their anatomical structures during surgical procedures. A vaginal manipulator is one such manipulator that can be introduced into a vagina for manipulating vaginal tissues. Several vaginal manipulators are available to help maneuver the vagina or vaginal walls, facilitating proper dissection in the pelvis. The purpose of some vaginal manipulators is to move the vagina around so that it is easier for dissection and placement of various medical devices such as implants. The vaginal manipulator may also act as a stabilizing backstop for suturing during abdominal/laparoscopic pelvic floor procedures.

Various shapes of vaginal manipulators are available to meet the requirements of surgery. Some existing manipulators used in pelvic surgeries are round or cylindrical in shape at their distal ends and are configured to contact the vaginal tissues. Other existing manipulators include flat or planar surfaces with rounded or curved end portions. With these known devices, however, it may be difficult to control or manipulate the cervix or the uterus when the vaginal manipulator is placed within the vagina of the patient. For example, the manipulator is placed within the vagina of the patient and is moved, the smooth or flat surfaces and the wet environment may cause or help cause the cervix or the uterus to slip or slide past the device as the device is moved within the body of the patient. Accordingly, it can be difficult to manipulate or move the cervix or uterus so that the cervix or the uterus can be in a desirable location during the medical procedure.

Thus, there is a need for an improved medical device or manipulator such as a vaginal manipulator that allows for or helps provide for the controlling or manipulating of the cervix or uterus.

SUMMARY

In one embodiment, a medical device includes an elongate member. The elongate member has a first end portion and a second end portion. The second end portion of the elongate member has an upper surface and a lower surface disposed opposite the upper surface. The lower surface has a planar portion. The upper surface has a planar portion and a concave portion.

In another embodiment, a medical device includes an elongate member having a first end portion and a second end portion opposite the first end portion. The first end portion includes an upper surface having a planar portion and a concave portion. The second end portion includes an upper surface having a planar portion and a concave portion.

In another embodiment, a method includes removing a cover member from an end portion of an elongate member to expose a concave portion, inserting the elongate member into a body of a patient, and engaging a concave portion of the elongate member with a portion of the body of the patient.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

In general, the invention is directed to systems, methods, and devices for treating female pelvic prolapse. However, the invention can be equally employed for other treatment purposes such as anal prolapse in males or females and for rectal manipulation during ano-rectosigmoid resections and other pelvic surgeries in which rectal manipulation is required. As described below in various illustrative embodiments, the invention provides systems, methods, and devices employing an improved manipulator configured to help maneuver the vagina facilitating proper dissection in the pelvis. The purpose of the vaginal manipulator is to move the vagina, cervix, and/or uterus around so that it is easier for dissection and placement of various implants into a patient's body. The vaginal manipulator may also acts as a backstop for suturing during abdominal/laparoscopic pelvic floor procedures.

The term patient may hereafter be used for a person who benefits from the medical device or the methods disclosed in the present invention. For example, the patient can be a person whose body is operated through the medical device or the method disclosed by the present invention. For example, in some embodiments, the patient may be a human female, a human male, or any other mammal.

Figure 1:
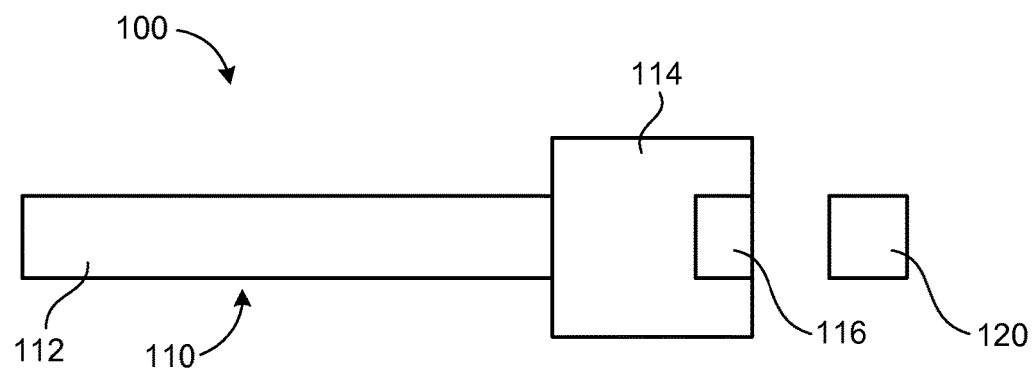
FIG. 1 is a schematic diagram of a medical device configured to manipulate a bodily tissue, in accordance with an embodiment of the invention.

FIG. 1 is a schematic diagram of a medical device 100 configured to manipulate a portion of a body of a patient such as bodily tissue or other member or portion of the body. The medical device 100 includes an elongated member 110. The elongate member has a first end portion 112 and a second end portion 114. In some embodiments, the first end portion 112 is disposed opposite the second end portion 114. In some embodiments, the elongate member 110 includes a shaft portion that is disposed between the first end portion 112 and the second end portion 114.

In some embodiments, the second end portion 114 of the medical device 100 includes surfaces that are configured to help maneuver the vagina to facilitate proper dissection in the pelvis. In some embodiments, flat surfaces of the end portion 114 are configured to move the vagina around so that it is easier for dissection and placement of implants such as suspension implant or devices such as the sacrocolpopexy mesh arms. Flat or planar surfaces of the second end portion 114 may also act as a backstop for suturing during abdominal/laparoscopic pelvic floor procedures. The flat surfaces can also be used to spread the bodily tissue to facilitate suturing at a correct location. In some embodiments, the medical practitioner may use a first flat surface to suture on anterior portions of the vagina and a second flat surface to suture on posterior portions of the vagina.

In the illustrated embodiment, the second end portion 114 includes a recess or concave portion 116. The recess or concave portion 116 may be of any size and shape. For example, the recess or concave portion 116 may be circular, rectangular, triangular, or any other shape. In some embodiments, the recess or concave portion 116 is disposed on a surface, such as an upper surface of the second end portion 114. In some embodiments, the recess or concave portion 116 is a cut out or step down from the remainder of the upper surface of the second end portion 114. In some embodiments, the upper surface includes a planar portion and the recess or concave portion 116.

In some embodiments, the recess or concave portion 116 is configured to engage a portion of the body of a patient when the medical device 100 is disposed within the body of the patient. For example, the recess or concave portion 116 may engage a portion of the body of a patient to grip or otherwise contact the portion of the body to help facilitate the control or manipulation of the portion of the body of the patient. For example, in some embodiments, the medical device 100 may be configured to be inserted into a vagina of the patient such that the second end portion 114 of the device 100 is disposed within the vagina of the patient. The recess or concave portion 116 may engage a cervix or portion of the cervix of the patient. The recess or concave portion 116 may also or alternatively engage a uterus or a portion of a uterus of the patient, such as a uterine stump of the patient. While the recess or concave portion 116 is engaged with the cervix, uterus, or other bodily portion, the medical device 100 may be manipulated or moved by a medical practitioner to manipulate or move the cervix, uterus, or other bodily portion.

In some embodiments, the recess or concave portion 116 includes a textured surface. In some embodiments, the textured surface is configured to help facilitate the engaging or gripping of the body portion such as the cervix or the uterus of the patient. For example, in some embodiments, the textured surface of the recess or concave portion 116 is a non-smooth surface. For example, in some embodiments, the surface of the recess or concave portion 116 includes bumps, ridges, dimples, or other non-smooth or uneven elements. In some embodiments a portion of or all of the vaginal manipulator comprises a coating to aid in the grippability of the device. For example, in some embodiments the device includes a coating such as a thermoplastic polymer coating.

In some embodiments, the recess or concave portion 116 includes sides or edges that are configured to help facilitate the engaging or gripping of the body portion. In some embodiments, the sides or edges may form a curved portion or hook portion that may help facilitate the engaging or gripping of the body portion.

In some embodiments, the second end portion includes projections that define a cut out or recess portion.

In some embodiments, the medical device 100 includes a cover or insert member 120. The cover or insert member 120 is configured to be removably coupled to the elongate member 110. For example, in some embodiments, the cover or insert member 120 is configured to be coupled to the recess or concave portion 116 of the second end portion 114. In some embodiments, the cover or insert member 120 is configured to cover or fill the recess or concave portion 116. In such embodiments, the cover or insert member 120 may be coupled to the recess or concave portion 116 to cause the second end portion 114 to have a more uniform surface.

In some embodiments, the cover or insert member 120 may be coupled to the elongate member 110 in situations where the medical practitioner does not desire to engage or otherwise control a bodily portion of the patient with the concave or recess portion 116. For example, a medical practitioner may not desire or need to control the cervix or uterus of a patient during a medical procedure on the patient if the patient has had a hysterectomy or otherwise does not have a uterus.

In some embodiments, the cover or insert member 120 may be removed from the elongate member 110 in situations where the medical practitioner desires to engage a bodily portion with the concave or recess member to move, manipulate, or control such bodily portion.

Any known coupling mechanism may be used to removably couple the cover or insert member 120 to the elongate member 110. For example, the cover or insert member 120 may include a coupling member and a the elongate member 110 may include a coupling member that is configured to engage the coupling member of the cover or insert member 120 to removably couple the cover or insert member 120 to the elongate member 110. For example, the cover or insert member 120 may be removably coupled to the elongate member via a tongue and groove system, a set of snaps, a set of magnets, Velcro or other coupling members. In some embodiments, the cover or insert member 120 is configured to be disposed within the recess or concave portion 116 and frictionally couple to the elongate member 210 within the recess or concave portion 116.

In some embodiments, the first end portion includes a recess or concave portion similar in structure and function to the recess or concave portion 116 of the second end portion 114. Accordingly, in such embodiments, either end portion may be inserted into a body of the patient to engage and manipulate bodily tissue with either of the recess or concave portions. In some embodiments, the recess or concave portion of the first end portion is larger or smaller than the recess or concave portion of the second end portion. For example, the recess or concave portion of the first end portion may be longer, wider, or deeper than the recess or concave portion of the second end portion. In such embodiments, a medical practitioner may insert the first end portion into the body of the patient or the second end portion into the body of the patient depending on the size of the bodily portion that the medical practitioner desires to engage with the recess or concave portions.

In some embodiments, the end portions are of different sizes or widths. Accordingly, a medical practitioner may insert the first end portion or the second end portion of the medical device into the body of the patient depending on the size of the patient or depending on the size of the opening into which the device will be inserted into. For example, in some embodiments, the lager end portion may be inserted into a patient that has a larger or wider vagina. Similarly, the smaller end portion may be inserted into a patient that has a smaller or narrower vagina.

In some embodiments, the medical device 100 includes two covers or insert members. One cover or insert member may be configured to be removably coupled to a recess or concave portion of the first end portion and the other cover or insert member may be configured to be removably coupled to a recess or concave portion of the second end portion.

In some embodiments, the medical device 100 includes or defines a lumen. The lumen is configured to receive a medical device that may be used to access and to move or otherwise manipulate a portion of the body of the patient. For example, in some embodiments, the medical device 100 may be inserted into a vagina of a patient and a uterine sound, medical tweezers, or another medical device may be inserted into the body of the patient via the lumen defined by the medical device 100. The uterine sound, medical tweezers, or other medical device may then be used to access a portion of the body. For example, the uterine sound, medical tweezers, or other medical device may be used to access or manipulate the uterus of the patient.

Figure 2:
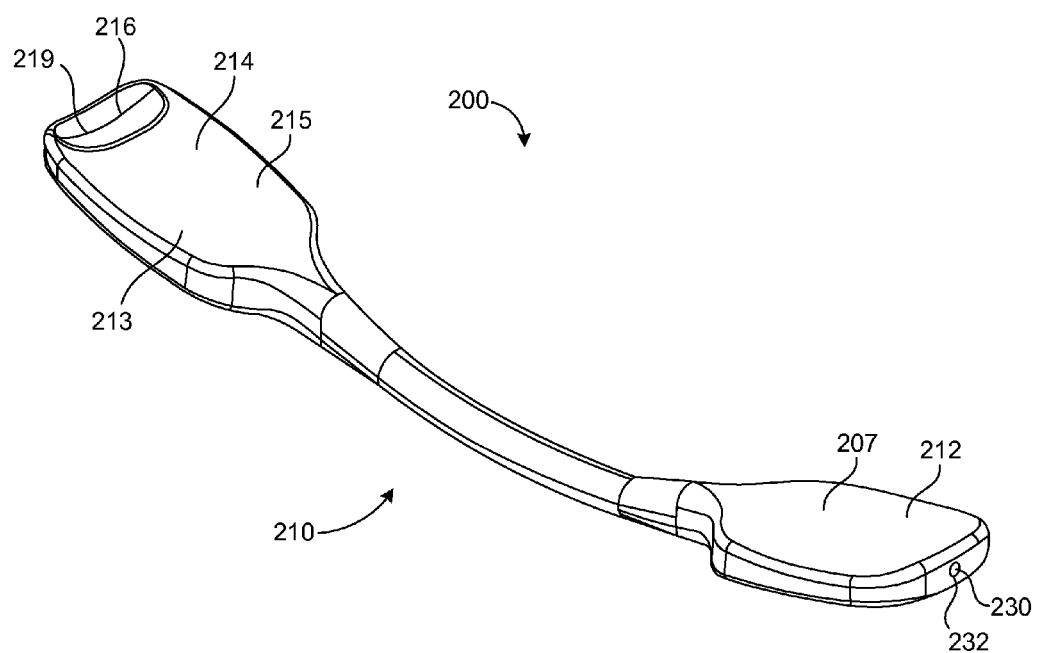
FIG. 2 is a perspective view of a medical device according to an embodiment of the invention.
Figure 3:
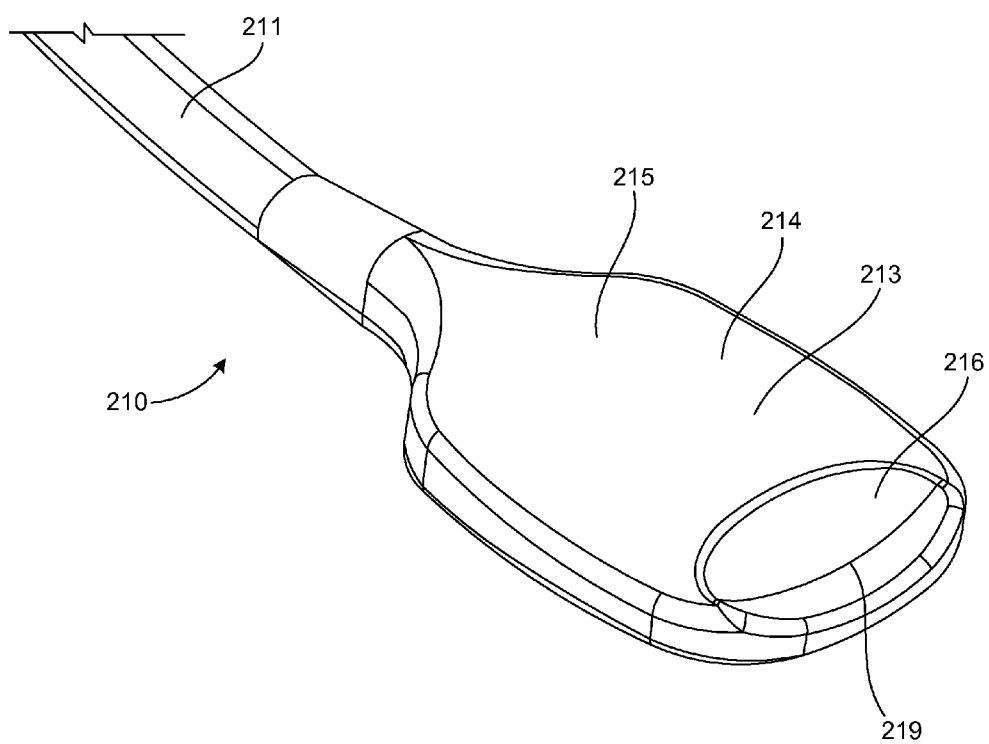
FIGS. 3-5 are perspective views of an end portion of the medical device of FIG. 2.
Figure 4:
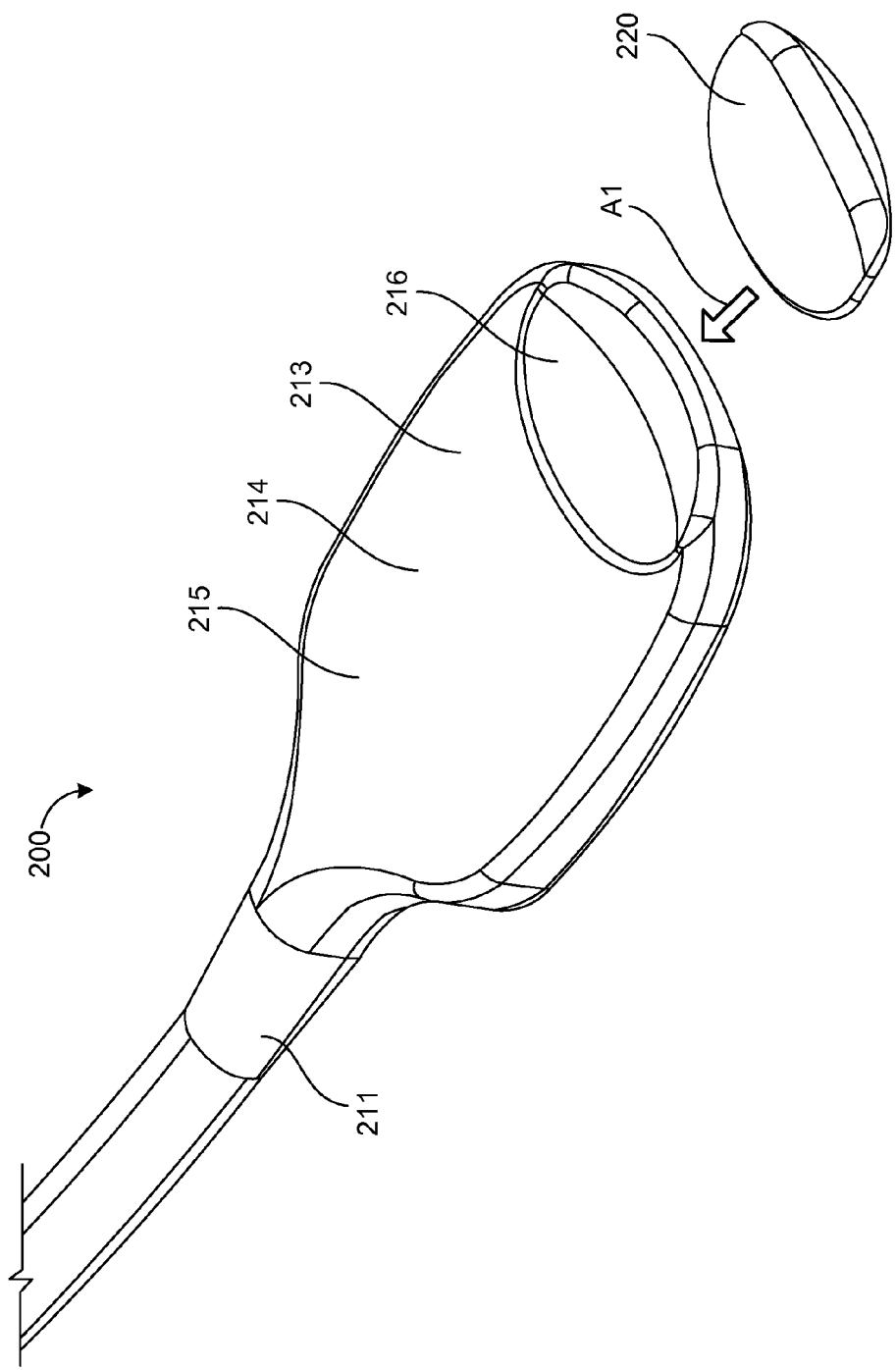
Figure 5:
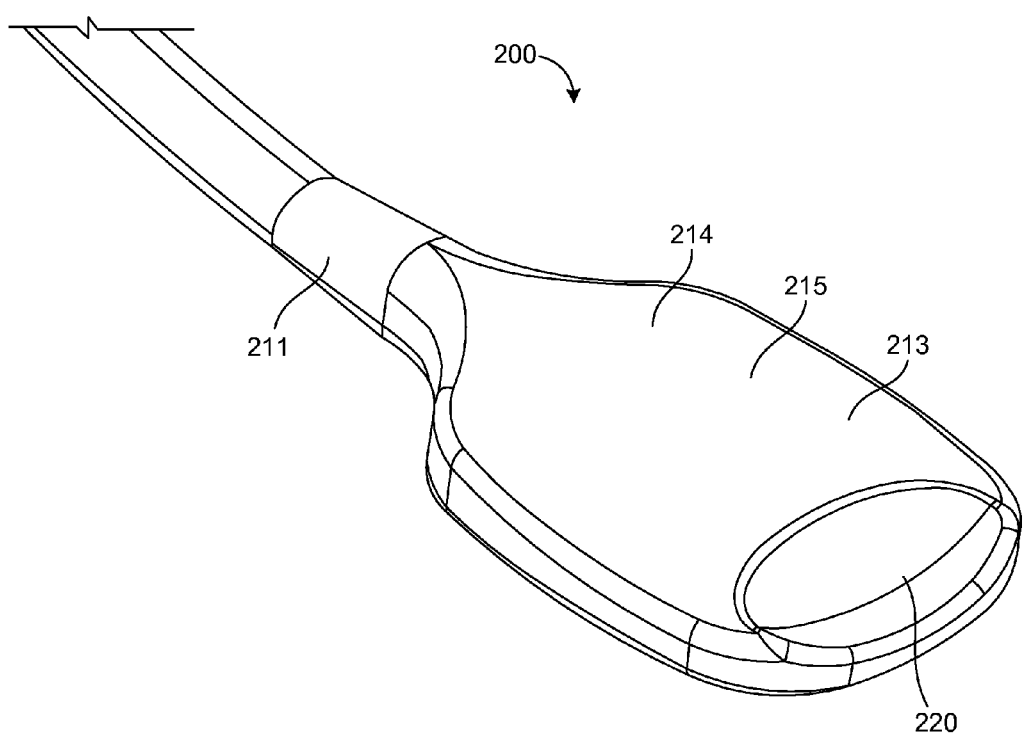
Figure 6:
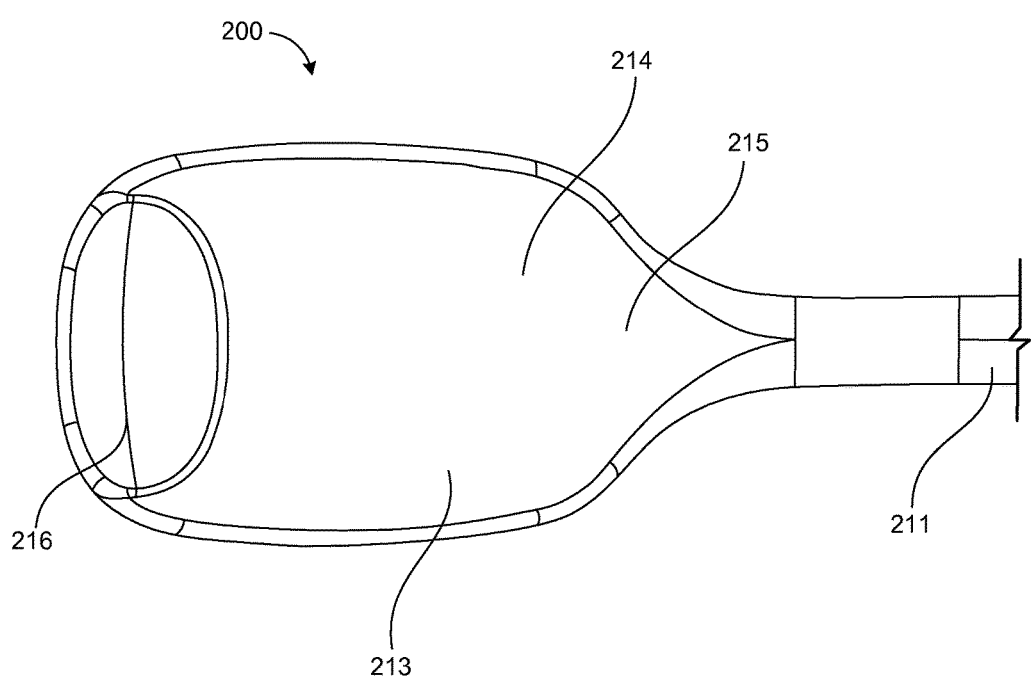
FIG. 6 is a top view of the end portion of the medical device of FIGS. 3-5.
Figure 7:
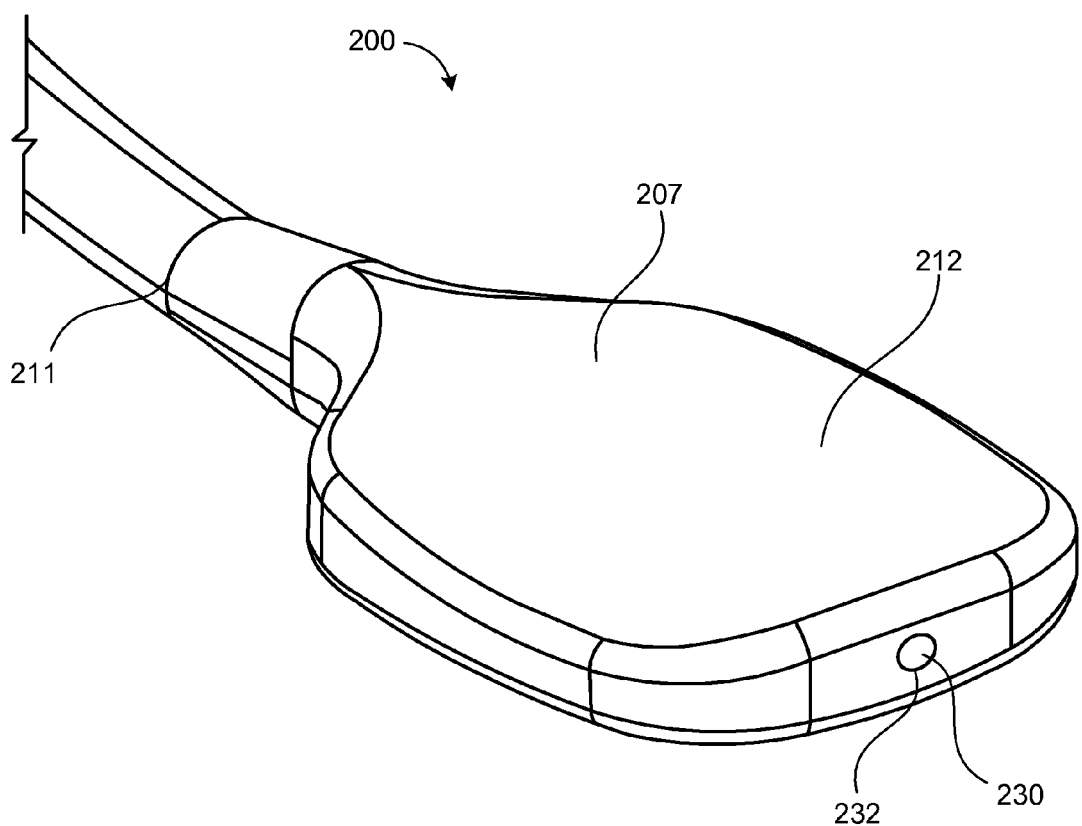
FIG. 7 is a perspective view of another end portion of the medical device of FIG. 2.
Figure 8:
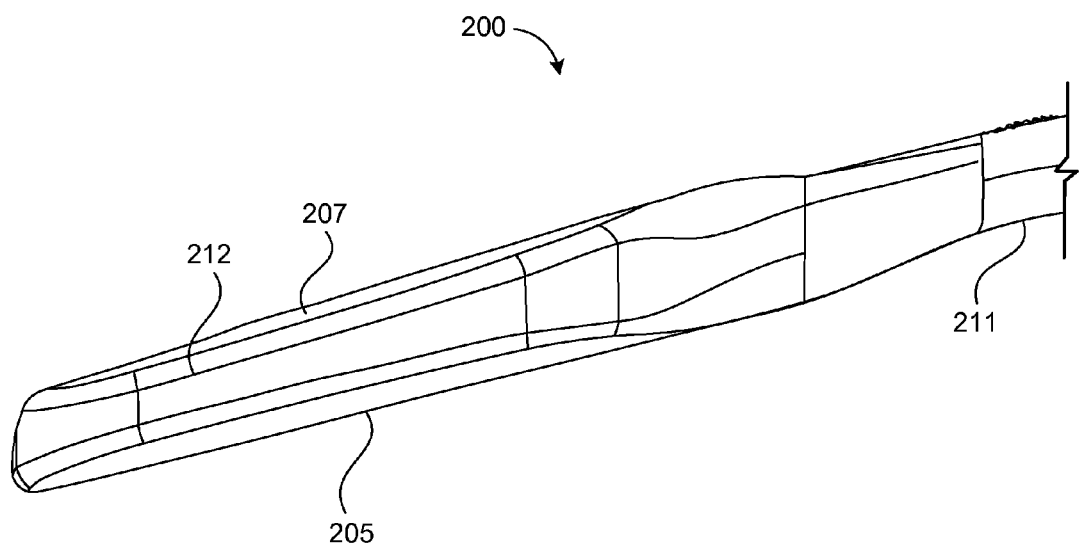
FIG. 8 is a side view of the end portion of FIG. 7.
Figure 9:
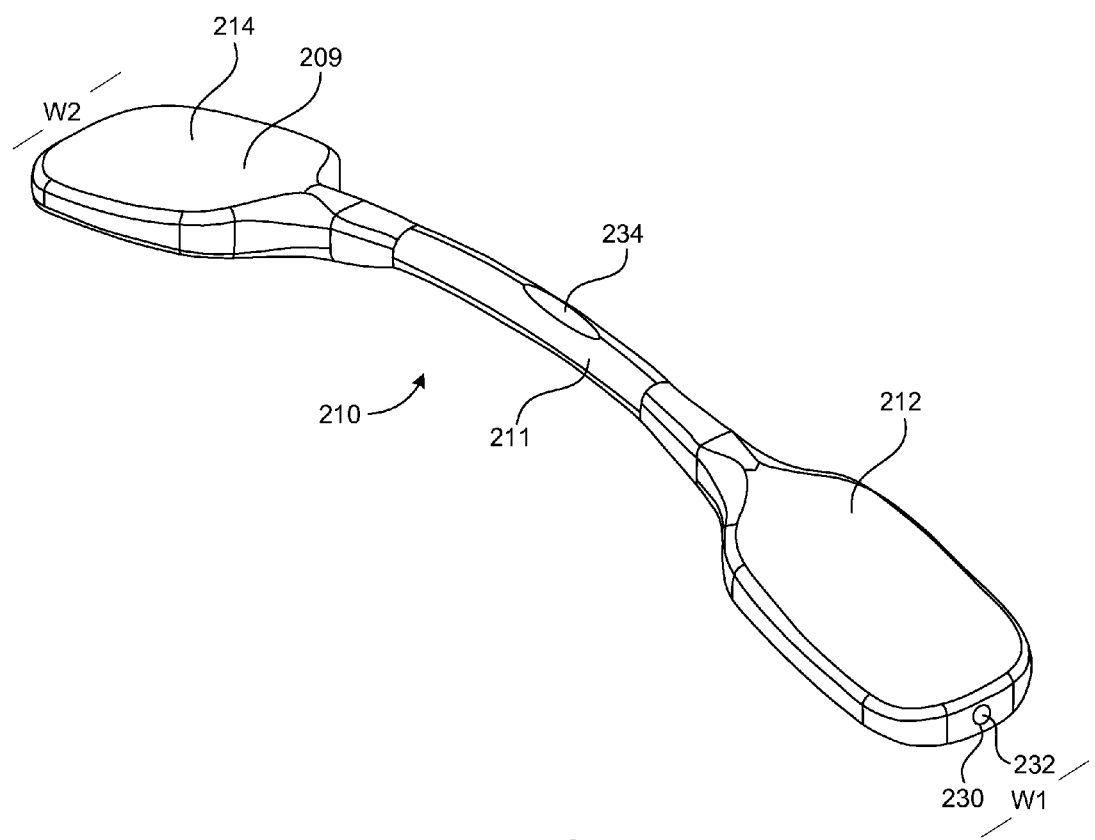
FIG. 9 is a perspective view of the medical device of FIG. 2.
Figure 10:
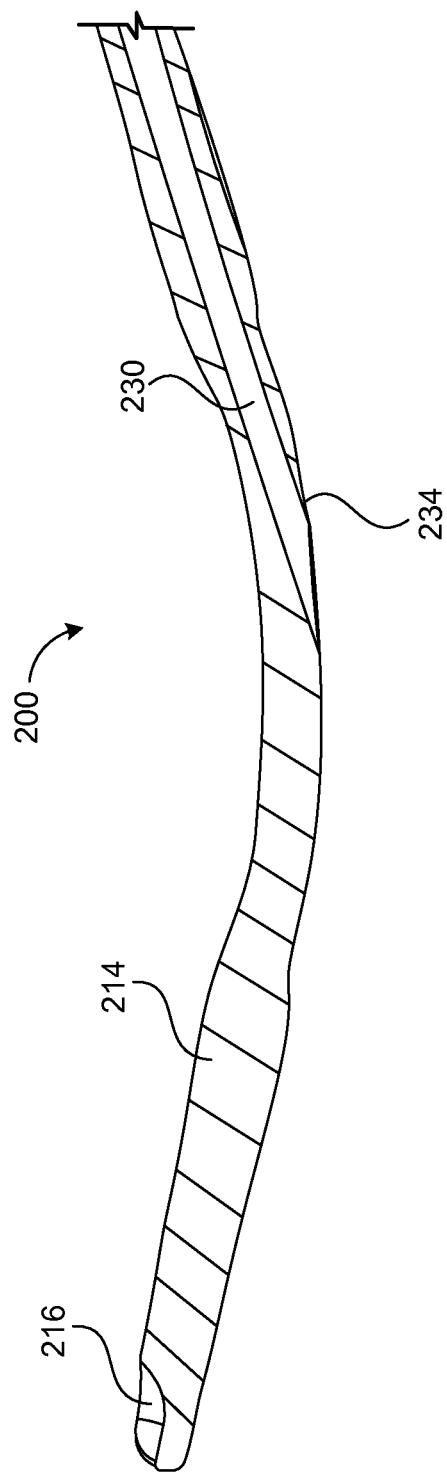
FIG. 10 is a cross sectional view of a portion of the medical device of FIG. 2.

FIGS. 2-10 illustrate a medical device 200 according to an embodiment of the invention. FIG. 2 is a perspective view of the medical device 200. FIGS. 3-5 are perspective views of an end portion of the medical device 200. FIG. 6 is a top view of the end portion of FIGS. 3-5. FIG. 7 is a perspective view of another end portion of the medical device 200. FIG. 8 is a side view of the end portion of FIG. 7. FIG. 9 is a perspective view of the medical device 200. FIG. 10 is a cross sectional view of a portion of the medical device 200.

The medical device 200 is configured to manipulate a portion of a body of a patient such as bodily tissue or other member or portion of the body. The medical device 200 includes an elongated member 210. The elongate member has a first end portion 212 and a second end portion 214. The first end portion 212 is disposed opposite the second end portion 214. The elongate member 210 includes a shaft portion 211 that is disposed between the first end portion 212 and the second end portion 214. In the illustrated embodiment, the first end portion 212 includes sides or surfaces that are flat or planar. The second end portion 214 includes one side that is flat or planar and another side that includes a concave portion.

The end portions 212 and 214 of the medical device 200 include surfaces that are configured to help maneuver or stretch the vagina to facilitate proper dissection in the pelvis or pelvic tissue. During medical procedures, either the first end portion 212 or the second end portion 214 may be inserted into the body of the patient.

In some embodiments, flat surfaces 207 of the first end portion 212 are configured to move the vagina around so that it is easier for dissection and placement of implants such as suspension implants or devices such as the sacrocolpopexy mesh arms. Flat or planar surfaces 207 of the first end portion 212 may also act as a backstop for suturing during abdominal/laparoscopic pelvic floor procedures. The flat surfaces 207 can also be used to spread the bodily tissue to facilitate suturing at a correct location. In some embodiments, the medical practitioner may use a first flat surface 207 to suture on anterior portions of the vagina and a second flat surface 205 to suture on posterior portions of the vagina. As best illustrated in FIG. 8, the first flat surface 207 is disposed opposite the second flat surface 205.

The second end portion 214 includes an upper surface 213 and a lower surface 209 disposed opposite the upper surface 213. The lower surface 213 includes a surface that is flat or planar.

The upper surface 213 of the second end portion 214 includes a surface that has a flat or planar portion 215 and a recess or concave portion 216. The recess or concave portion 216 may be of any size and shape. For example, the recess or concave portion 216 may be circular, rectangular, triangular, or any other shape. The recess or concave portion 216 is a cut out or step down from the remainder of the upper surface of the second end portion 214. Specifically, the recess or concave portion 216 is a cut out or step down from the flat or planar portion 215.

In some embodiments, the recess or concave portion 216 is configured to engage a portion of the body of a patient when the medical device 200 is disposed within the body of the patient. For example, the recess or concave portion 216 may engage a portion of the body of a patient to grip or otherwise contact the portion of the body to help facilitate the control or manipulation of the portion of the body of the patient. For example, in some embodiments, the medical device 200 may be configured to be inserted into a vagina of the patient such that the second end portion 214 of the device 200 is disposed within the vagina of the patient. The recess or concave portion 216 may engage a cervix or portion of the cervix of the patient. The recess or concave portion 216 may also or alternatively engage a uterus or a portion of a uterus of the patient, such as a uterine stump of the patient. While the recess or concave portion 216 is engaged with the cervix, uterus, or other bodily portion, the medical device 200 may be manipulated or moved by a medical practitioner to manipulate or move the cervix, uterus, or other bodily portion.

In some embodiments, the recess or concave portion 216 includes a textured surface. In some embodiments, the textured surface is configured to help facilitate the engaging or gripping of the body portion such as the cervix or the uterus of the patient. For example, in some embodiments, the textured surface of the recess or concave portion 216 is a non-smooth surface. For example, in some embodiments, the surface of the recess or concave portion 216 includes bumps, ridges, dimples, or other non-smooth or uneven elements. In some embodiments a portion of or all of the vaginal manipulator comprises a coating to aid in the grippability of the device. For example, in some embodiments the device includes a coating such as a thermoplastic polymer coating.

In the illustrated embodiment, the recess or concave portion 216 includes or defines a slot or ridge 219. The slot or ridge provides texture to the surface of the recess or concave portion 216. The recess or concave portion 216 may also include other surface features to provide texture to the surface of the recess or concave portion 216.

The medical device 200 includes a cover or insert member 220. The cover or insert member 220 is configured to be removably coupled to the elongate member 210. The cover or insert member 220 is configured to be coupled to the recess or concave portion 216 of the second end portion 214. For example, as best illustrated in FIG. 4, the cover or insert member 220 may be moved in the direction of arrow A1 to couple the cover or insert member to the elongate member 210. In some embodiments, the cover or insert member 220 is sized and shaped to cover or fill the recess or concave portion 216. In such embodiments, the cover or insert member 220 may be coupled to the recess or concave portion 216 to cause the second end portion 214 to have a more uniform surface.

In some embodiments, the cover or insert member 220 may be coupled to the elongate member 210 in situations where the medical practitioner does not desire to engage or otherwise control a bodily portion of the patient with the concave or recess portion 216. For example, a medical practitioner may not desire or need to control the cervix or uterus of a patient during a medical procedure on the patient if the patient has had a hysterectomy or otherwise does not have a uterus.

In some embodiments, the cover or insert member 220 may be removed from the elongate member 210 in situations where the medical practitioner desires to engage a bodily portion with the concave or recess member to move, manipulate, or control such bodily portion.

Any known coupling mechanism may be used to removably couple the cover or insert member 220 to the elongate member 210. For example, the cover or insert member 220 may include a coupling member and a the elongate member 210 may include a coupling member that is configured to engage the coupling member of the cover or insert member 220 to removably couple the cover or insert member 220 to the elongate member 210. For example, the cover or insert member 220 may be removably coupled to the elongate member via a tongue and groove system, a set of snaps, a set of magnets or other coupling members. In some embodiments, the cover or insert member 220 is configured to be disposed within the recess or concave portion 216 and frictionally couple to the elongate member within the recess or concave portion 216.

In the illustrated embodiment, the slot or ridge 219 may engage a coupling portion (not illustrated) of the cover or insert member 220 to removably couple the cover or insert member to the elongate member 210.

The medical device 200 includes or defines a lumen 230. The lumen 230 is configured to receive a medical device that may be used to access and to move or otherwise manipulate a portion of the body of the patient. For example, in some embodiments, the medical device 200 may be inserted into a vagina of a patient and an endoscope, needle, biopsy forceps, uterine sound, medical tweezers, catheter or another medical device may be inserted into the body of the patient via the lumen 230 defined by the medical device 200. The endoscope, needle, biopsy forceps, uterine sound, medical tweezers, catheter or other medical device may then be used to access a portion of the body. For example, the endoscope, needle, biopsy forceps, uterine sound, medical tweezers, catheter or other medical device may be used to access or manipulate the uterus of the patient.

In the illustrated embodiment, the lumen 230 extends from the first end portion 212 to a location on the shaft portion 211. Specifically, the first end portion 212 defines an opening 232 that is in communication with the lumen 230. Similarly, the shaft portion 211 defines an opening 234 that is in communication with the lumen 230. Accordingly, the lumen 230 extends from the opening 232 defined by the first end portion 212 to the opening 234 defined by the shaft portion 211. The medical device 200 may be inserted into a patient such that the first end portion 212 is disposed within the vagina of the patient. A medical device, such as an endoscope, needle, biopsy forceps, uterine sound, medical tweezers, catheter, or other medical device may then be inserted into the lumen and extend through the opening 232 defined by the first end portion 212 and the opening 234 defined by the shaft portion 211. The medical device, such as the endoscope, needle, biopsy forceps, uterine sound, catheter or medical tweezers may then be used to engage bodily tissue such as the uterus or cervix of the patient. Alternatively, opening 234 could be located at the far opposite end of the device. In such an embodiment, the lumen 230 would extend the length or substantially the length of the device. In some embodiments entrance 234 is sized and shaped to promote access into the lumen 230 by, for example, having a funnel shape with the smaller end entering the lumen 230 (or disposed proximate the lumen).

In the illustrated embodiment, the lumen 230 is straight or linear or substantially straight or linear. In other embodiments, the lumen 230 is curved or bent. In some embodiments, the lumen may extend from the first end portion of the medical device to the second end portion of the medical device.

In the illustrated embodiment, the shaft portion 211 is bent or curved. Specifically, the shaft portion 211 may have a bend or curve of a few degrees. In some embodiments, the shaft portion 211 bends or curves to form an angle of between 120 degrees to 175 degrees. In other embodiments, the shaft portion 211 is linear or straight.

Figure 11:
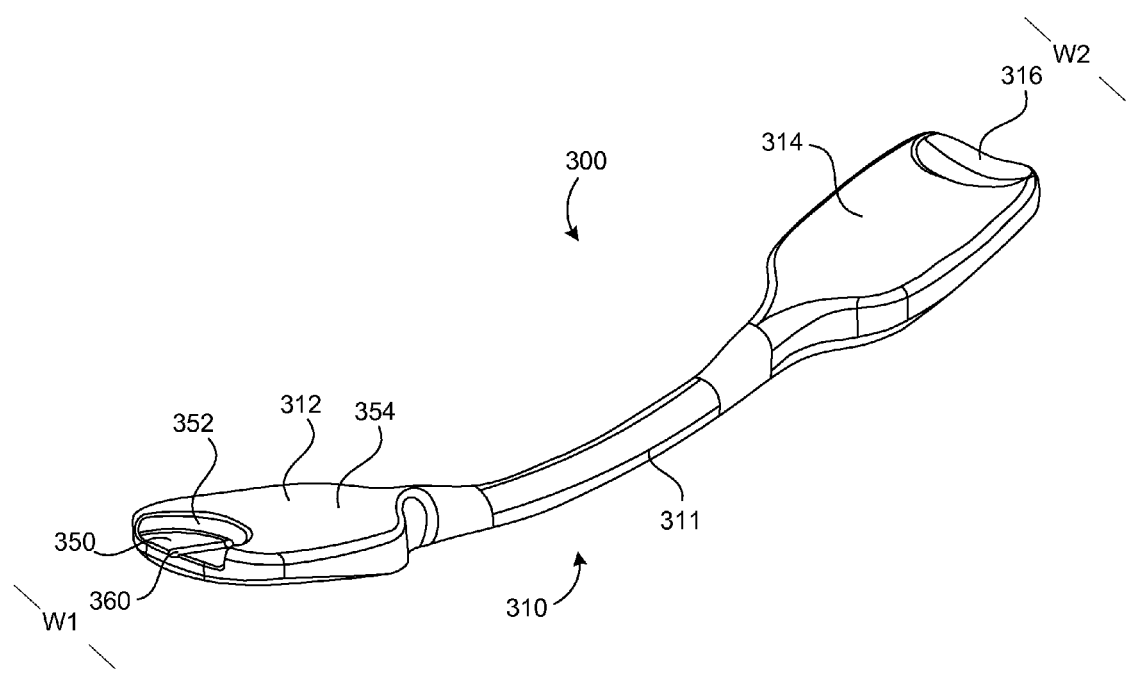
FIG. 11 is a perspective view of a medical device according to another embodiment of the invention.

FIG. 11 is a perspective view of a medical device 300 according to an embodiment of the invention. The medical device 300 includes an elongated member 310. The elongate member 310 has a first end portion 312 and a second end portion 314. The first end portion 312 is disposed opposite the second end portion 314. The elongate member 310 includes a shaft portion 311 that is disposed between the first end portion 312 and the second end portion 314.

The end portions 312 and 314 of the medical device 300 include surfaces that are configured to help maneuver or stretch the vagina to facilitate proper dissection in the pelvis or pelvic tissue. During medical procedures, either the first end portion 312 or the second end portion 314 may be inserted into the body of the patient.

In the illustrated embodiment, the second end portion 314 includes a recess or concave portion 316. The recess or concave portion 316 may be of any size and shape. For example, the recess or concave portion 316 may be circular, rectangular, triangular, or any other shape. In the illustrated embodiment, the recess or concave portion 316 is disposed on a surface, such as an upper surface of the second end portion 314. The recess or concave portion 316 is a cut out or step down from the remainder of the upper surface of the second end portion 314. In the illustrated embodiment, the upper surface includes a planar portion and the recess or concave portion 316. The recess or concave portion 316 may be symmetrical about a longitudinal axis of the medical device 300.

The recess or concave portion 316 is configured to engage a portion of the body of a patient when the medical device 300 is disposed within the body of the patient. For example, the recess or concave portion 316 may engage a portion of the body of a patient to grip or otherwise contact the portion of the body to help facilitate the control or manipulation of the portion of the body of the patient. For example, in some embodiments, the medical device 300 may be configured to be inserted into a vagina of the patient such that the second end portion 314 of the device 300 is disposed within the vagina of the patient. The recess or concave portion 316 may engage a cervix or portion of the cervix of the patient. The recess or concave portion 316 may also or alternatively engage a uterus or a portion of a uterus of the patient, such as a uterine stump of the patient. While the recess or concave portion 316 is engaged with the cervix, uterus, or other bodily portion, the medical device 300 may be manipulated or moved by a medical practitioner to manipulate or move the cervix, uterus, or other bodily portion.

The first end portion 312 includes a recess 350. The recess 350 is similar to the recess or concave portion 316 of the second end portion 314. The recess 350 is a step down or cut out from the flat or planar portion or surface of the first end portion 312. The recess 350 is configured to grip or receive the cervix or the uterus (similar to the recess or concave portion 316 of the second end portion 314) when the first end portion 312 is disposed within a vagina of a patient.

In the illustrated embodiment, the recess 350 is defined by a side wall 352. The side wall 352 is perpendicular or substantially perpendicular to the flat or planar portion 354 of the first end portion 312. The side wall 352 is curved. In other embodiments, the side wall is linear or formed or several linear portions.

In some embodiments, the medical device 300 includes a covers or insert members. For example, the medical device may include a first cover or insert member and a second cover or insert member. The covers or insert members may be configured to be removably coupled to the elongate member 310. For example, in some embodiments, the covers or insert members may be configured to be coupled to the recesses or concave portions 316 and 350 of the end portion 314 and 312. In some embodiments, the covers or insert members are configured to cover or fill the recesses or concave portions. In such embodiments, the covers or insert members may be coupled to the recesses or concave portions to cause the end portions to have a more uniform surface.

In some embodiments, the recess or concave portion of the first end portion is larger or smaller than the recess or concave portion of the second end portion. For example, the recess or concave portion of the first end portion may be longer, wider, or deeper than the recess or concave portion of the second end portion. In such embodiments, a medical practitioner may insert the first end portion 312 into the body of the patient or the second end portion 314 into the body of the patient depending on the size of the bodily portion that the medical practitioner desires to engage with the recess or concave portions.

In some embodiments, the end portions are of different sizes or widths. Accordingly, a medical practitioner may insert the first end portion 312 or the second end portion 314 of the medical device 300 into the body of the patient depending on the size of the patient or depending on the size of the opening into which the device will be inserted into. For example, in some embodiments, the lager end portion may be inserted into a patient that has a larger or wider vagina. Similarly, the smaller end portion may be inserted into a patient that has a smaller or narrower vagina. In the illustrated embodiment, the first end portion 312 has a width of W1 and the second end portion 314 has a width of W2. In some embodiments, W1 is greater than W2. In other embodiments, W2 is greater than W1. In some embodiments, W1 is the same as W2.

The medical device 300 includes or defines a lumen 360. The lumen is configured to receive a medical device that may be used to access and to move or otherwise manipulate a portion of the body of the patient. For example, in some embodiments, the medical device 300 may be inserted into a vagina of a patient and an endoscope, needle, biopsy forceps, uterine sound, medical tweezers, catheter or another medical device may be inserted into the body of the patient via the lumen 360 defined by the medical device 300. The endoscope, needle, biopsy forceps, uterine sound, medical tweezers, catheter or other medical device may then be used to access a portion of the body. For example, the uterine sound, medical tweezers, or other medical device may be used to access or manipulate the uterus of the patient.

In the illustrated embodiment, the recess 350 or the surface of the recess 350 defines a portion of the lumen 360. In other words, the lumen 360 extends through a portion of the recess 350 of the first end portion 312.

Figure 12:
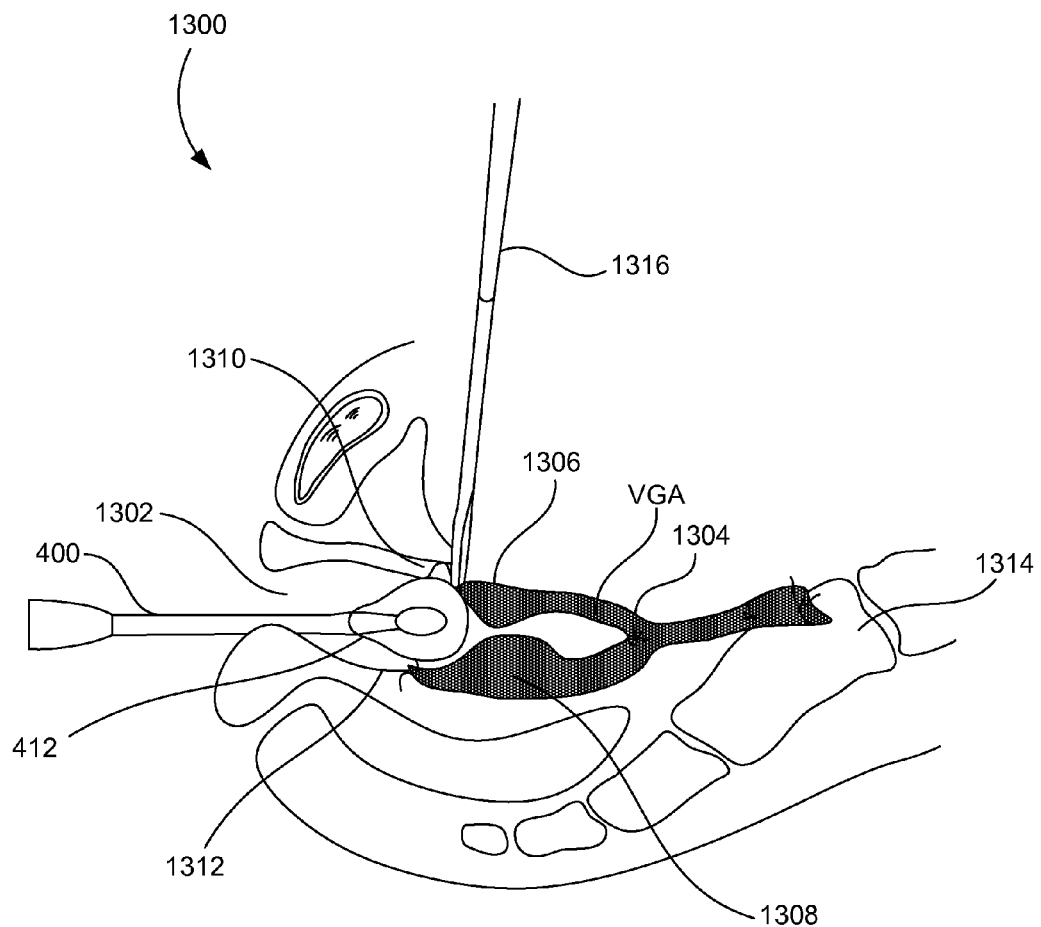
FIGS. 12 and 13 are schematic views of a medical device disposed within a body of a patient.

FIG. 12 schematically illustrates placement of a medical device 400 inside a vagina for manipulation of bodily tissues. The medical device 400 may be similar to the other devices disclosed herein. As shown, one of the flat surfaces can be used to manipulate the tissues. The flat surfaces, such as 412 assist in moving the vagina 1302 around so that it is easier for dissection and placement of a bodily implant 1304 into a patient's body. The flat surfaces 412 also act as a backstop for suturing during abdominal/laparoscopic pelvic floor procedures. The flat surface 412 can also be used to spread the bodily tissue to facilitate suturing at a correct location.

In some embodiments, the implant 1304 includes a first elongated member 1306 and a second elongated member 1308. A first end portion of the first elongated member 1206 is attached to an anterior vaginal wall 1310 and a second end portion of the first elongated member 1306 is attached to a sacrum 1314 or tissues disposed proximate the sacrum 1314. A first end portion of the second elongated member 1308 is attached to a posterior vaginal wall 1312 and a second end portion of the second elongated member 1308 is attached to the sacrum 1314 or tissues disposed proximate the sacrum 1314. In the illustrated, embodiment, the implant 1304 surrounds or cups the distal portion of the vagina (such as the vaginal apex VGA). The medical device 400 may be disposed within the body of the patient such that the medical device 400 is contacting or disposed adjacent to the vaginal apex VGA. Additionally, a delivery device 1316 configured to make incisions and hold a suture during surgery is also depicted. In some embodiments, the delivery device 1316 can be a surgical needle.

While FIG. 12 illustrates the use of the medical device 400 while placing an implant 1304 that has particular portions and a shape, a Y-shape, the medical device 400 may be used in a procedure to place or implant any type of implant. For example, the medical device 400 may be used to place a single linear or rectangular shaped implant. In some embodiments, the medical device 400 may be used to place a plurality of linear or rectangular shaped implants.

Additionally, while FIG. 12 illustrates the medical device 400 disposed within a vagina, in other embodiments, the medical device 400 may be used in other locations within the body, such as a within a rectum of a patient, a bladder of a patient, or within a gastrointestinal tract of a patient.

Figure 13:
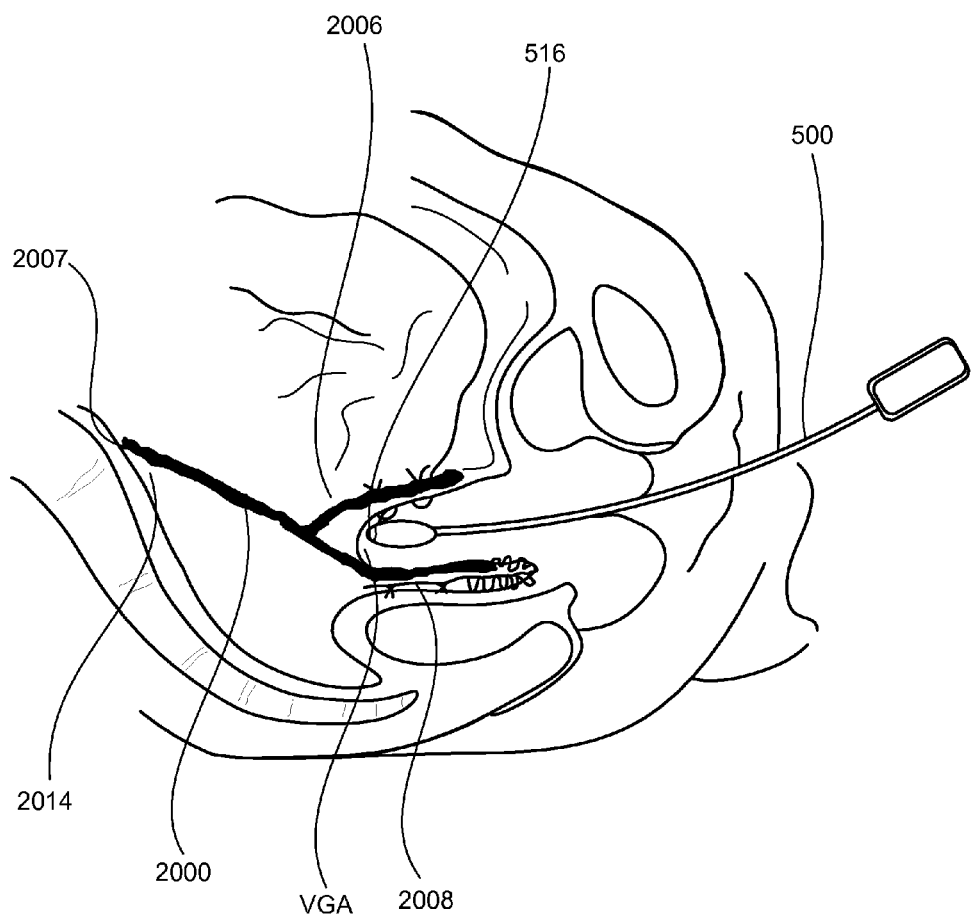

FIG. 13 schematically illustrates a medical device 500 disposed within a body of a patient. The medical device 500 may be similar to the other devices disclosed herein. As illustrated, in some embodiments, the implant 2000 may be a Y-shaped implant. In such embodiments, the Y-shaped implant 2000 includes a first elongated member 2006 and a second elongated member 2008 that extends from a mid-portion of the first elongated member 2006. A first end portion 2005 of the first elongated member 2006 can be attached to an anterior vaginal wall and a second end portion 2007 of the first elongated member 2006 can attached to a sacrum 2014 of the patient or tissues disposed proximate the sacrum 2014 of the patient. A first end portion 2009 of the second elongated member 2008 is attached to a posterior vaginal wall. For example, in the illustrated embodiment, the implant 2000 may form such a Y-shaped implant as the first elongated member 2006 may be coupled to the second elongated member 2008 at or near the junction of the members (for example, near the vaginal apex VGA of the patient). As illustrated, the implant 2000 may surround or cup the vaginal apex VGA. Additionally, the device 1900 may be disposed within the body of the patient such that an end portion of the device 1900 is in contact with or disposed adjacent the vaginal apex VGA.

As schematically illustrated, the medical device 500 may include an end portion that has or defines a recess or concave portion 516. The recess or concave portion may be configured to engage or receive a portion of the body of the patient or bodily tissue. For example, in some embodiments, the recess or concave portion 516 may be configured to engage or receive a portion of the cervix or uterus of the patient. The medical device 500 may then be used to move or manipulate the cervix or uterus of the patient (or other bodily portion) during a medical procedure.

Figure 14:
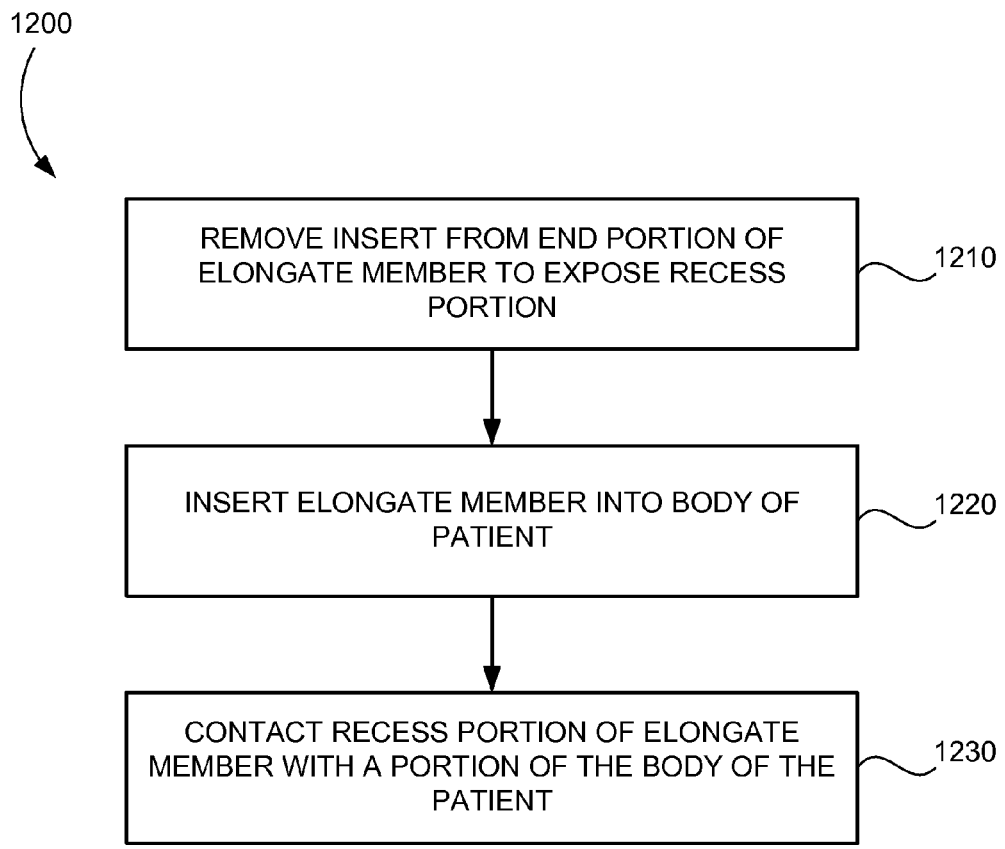
FIG. 14 is a flow chart of a method according to an embodiment of the invention.

FIG. 14 is a method 1200 according to an embodiment of the invention. At 1210, a cover or insert member is removed from an elongate member of a medical device. For example, a medical practitioner may remove the cover or insert member prior to a medical procedure on a patient that has a uterus.

At 1220, the elongate member is inserted within the body such that a recess portion or concave portion is disposed within the body of the patient. In some embodiments, the elongate member is inserted into a vagina of a patient. In other embodiments, the elongate member is disposed or inserted into a different portion of the body of the patient.

At 1230, the recess portion is contacted or engaged with a portion of the body of the patient. For example, the medical practitioner may move the elongate member within the body of the patient to contact or engage the recess with a portion of the body of the patient. In some embodiments, a cervix or uterus of the patient is contacted, engaged, or otherwise received by the recess portion.

In some embodiments, once the bodily portion is engaged by the recess portion, the medical practitioner may move the elongate member to manipulate or move the bodily portion. For example, the medical practitioner may move the cervix or portion of the uterus out of the way of a medical procedure. In other embodiments, the bodily portion may be moved or manipulated differently.

In some embodiments, another medical instrument is inserted within the body of the patient via a lumen defined by the medical device. For example, a endoscope, needle, biopsy forceps, uterine sound, medical tweezers, catheter or other medical instrument may be inserted though a lumen defined by the elongate member of the medical device to engage and manipulate a portion of the body of the patient. For example, in some embodiments, the uterine sound or other medical instrument may be used to engage and manipulate the uterus of the patient.

In some embodiments, the cover or insert member may be coupled to the elongate member prior to inserting the elongate member into the body of the patient. For example, if the patient does not have a uterus, the recess may not be required and the cover or insert member may be coupled to the elongate member to cover or fill the recess.

In some embodiments, the medical device includes end portions of different sizes or widths. The medical practitioner may determine which side or end portion to insert into the body of the patient based on the size of the patient or the size of the opening being used to insert the device into the body of the patient.

In some embodiments, a medical device includes an elongate member having a first end portion and a second end portion, the second end portion having an upper surface and a lower surface disposed opposite the upper surface, at least one of the surfaces having a planar portion and a concave portion.

In some embodiments, the concave portion has a textured surface. In some embodiments, the concave portion is configured to receive at least a portion of a bodily organ or anatomical feature when the medical device is placed within a body of a patient. In some embodiments, the organ or anatomical feature is a cervix or a portion of a uterus.

In some embodiments, the elongate member defines a lumen.

In some embodiments, the elongate member defines a lumen, the first end portion defines an opening that is in communication with the lumen. In some embodiments, the elongate member includes a shaft portion disposed between the first end portion and the second end portion, the elongate member defining a lumen extending from the first end portion to the shaft portion.

In some embodiments, the elongate member includes a shaft portion disposed between the first end portion and the second end portion, the elongate member defining a lumen extending from an opening defined by the first end portion to an opening defined by the shaft portion. In some embodiments, the first end portion has an upper surface and a lower surface disposed opposite the upper surface, wherein at least one of the surfaces includes a planar portion and a concave portion.

In some embodiments, the first end portion has a width, the second end portion has a width, the width of the second end portion being greater than the width of the first end portion.

In some embodiments, the device further include a cover member, the cover member configured to be removably coupled to the second end portion.

In some embodiments, the medical device further includes a cover member, the cover member configured to be removably coupled to the concave portion of the upper surface of the second end portion.

In some embodiments, a medical device, includes an elongate member having a first end portion and a second end portion opposite the first end portion, the first end portion having a surface including a planar portion and a concave portion, the second end portion having a second surface including a planar portion and a concave portion.

In some embodiments, the concave portion of the first end portion has a textured surface. In some embodiments, the concave portion of the first end portion is configured to receive at least a portion of a body organ or anatomical feature when the first end portion of the medical device is placed within a body of a patient. In some embodiments, the elongate member defines a lumen.

In some embodiments, the elongate member defines a lumen, the first end portion defines an opening that is in communication with the lumen.

In some embodiments, the elongate member includes a shaft portion disposed between the first end portion and the second end portion, the elongate member defining a lumen extending from the first end portion to the shaft portion.

In some embodiments, the elongate member includes a shaft portion disposed between the first end portion and the second end portion, the elongate member defining a lumen extending from an opening defined by the first end portion to an opening defined by the shaft portion.

In some embodiments, a method, includes removing a cover member from an end portion of an elongate member to expose a concave portion; inserting the elongate member into a body of a patient; and engaging a concave portion of the elongate member with a portion of the body of the patient.

In some embodiments, the inserting includes inserting the elongate member into a vagina of the patient and the engaging includes engaging the concave portion of the elongate member with a portion of a cervix of the patient or a portion of a uterus of the patient.

While certain features of the described implementations have been illustrated as described herein, many modifications, substitutions, changes and equivalents will now occur to those skilled in the art. It is, therefor, to be understood that the appended claims are intended to cover all such modifications and changes as fall within the scope of the embodiments.

What is claimed is:

1. A medical device, comprising:
an elongate member having a shaft, a first end portion, and a second end portion, the shaft being disposed between the first end portion and the second end portion, the shaft having a curved portion, the second end portion having a width larger than a width of the shaft, the second end portion configured to be inserted into a vagina of a patient,
the second end portion having a first surface and a second surface disposed opposite the first surface, the first surface having a planar portion and a concave portion, the concave portion being recessed from the planar portion of the first surface, the second end portion having a cutout that exposes the concave portion, the concave portion extending to a terminal end of the elongate member,
the concave portion configured to engage a cervix or uterus when the medical device is placed within a body of a patient; and
a cover member, the cover member configured to be removably coupled to the concave portion, the cover member configured to fill the concave portion.

2. The medical device of claim 1, wherein the concave portion has a textured surface to facilitate the engaging of the cervix or uterus.

3. The medical device of claim 1, wherein the second surface of the second end portion is planar, the second surface of the second end portion being devoid of a concave portion that is recessed from the second surface.

4. The medical device of claim 1, wherein the elongate member defines a lumen.

5. The medical device of claim 1, wherein the elongate member defines a lumen, the first end portion defines a first opening, and the shaft defines a second opening, wherein the first and second openings are in communication with the lumen.

6. The medical device of claim 1, wherein the curved portion of the shaft forms an angle between 120 degrees to 175 degrees.

7. The medical device of claim 1, wherein the concave portion defines a ridge.

8. The medical device of claim 1, wherein the first end portion has a first surface and a second surface disposed opposite the first surface, wherein the first surface of the first end portion includes a planar portion and a concave portion, the concave portion of the first end portion being recessed from the planar portion of the first surface of the first end portion.

9. The medical device of claim 1, wherein a width of the first end portion is greater than the width of the shaft, and the width of the second end portion is greater than the width of the first end portion.

10. The medical device of claim 1,
wherein the cover member is configured to be inserted into the concave portion, wherein the cover member has a portion that lies in a same plane as the planar portion when the cover member is inserted into the concave portion.

11. A medical device, comprising:
an elongate member having a shaft, a first end portion, and a second end portion opposite the first end portion, the shaft being disposed between the first end portion and the second end portion, the shaft having a curved portion, the shaft defining a lumen, the second end portion having a width larger than a width of the shaft,
the first end portion having a surface including a first planar portion and a first concave portion, the first end portion defining a first thickness at a first location and a second thickness at a second location, the first concave portion being recessed from the first planar portion of the surface of the first end portion, the first concave portion extending from the first location and the second location, the first concave portion extending to a terminal end of the first end portion, the first end portion defining an opening that is in communication with the lumen,
the second end portion having a surface including a second planar portion and a second concave portion, the second concave portion being recessed from the second planar portion of the surface of the second end portion.

12. The medical device of claim 11, wherein the first concave portion of the first end portion has a textured surface.

13. The medical device of claim 11, wherein the first concave portion of the first end portion is configured to engage a cervix or uterus when the medical device is placed within a body of a patient.

14. The medical device of claim 11, wherein the elongate member defines a lumen.

15. The medical device of claim 11, wherein the lumen extends from the opening defined by the first end portion to an opening defined by the shaft.

16. A method, comprising:
removing a cover member from a first end portion of an elongate member to expose a concave portion defined by the first end portion, the first end portion having a width larger than a width of a shaft of the elongate member, the first end portion having a flat surface, the concave portion being recessed from the flat surface of the first end portion, the shaft having a curved portion, the elongate member having a second end portion, the shaft being disposed between the first end portion and the second end portion, the concave portion extending to a terminal end of the elongate member, the elongate member defining a lumen, the first end portion defining an opening, the opening being in communication with the lumen;

inserting the elongate member into a body of a patient; and engaging the concave portion with a cervix or uterus within the body of the patient.

17. The method of claim 16, wherein the second end portion has a width larger than the width of the shaft.

18. A medical device, comprising:

an elongate member having a shaft, a first end portion, and a second end portion, the shaft being disposed between the first end portion and the second end portion defining a longitudinal axis, the shaft having a curved portion, the second end portion having a first side end portion and a second side end portion defining a width, the width of the second end portion being larger than a width of the shaft, the second end portion having a first surface and a second surface disposed opposite the first surface, the first surface having a planar portion and a concave portion, the concave portion being recessed from the planar portion of the first surface, the second end portion having a cutout defined by an edge that exposes the concave portion, the cutout being configured to be extended towards the first side end portion and the second side end portion of the second end portion in a direction orthogonal to the longitudinal axis; and a cover member, the cover member configured to be removably coupled to the concave portion, the cover member configured to fill the concave portion.

* * * * *